United States Patent

Whitehead

Patent Number: 6,030,637
Date of Patent: Feb. 29, 2000

[54] PELLET FOR ADMINISTRATION TO RUMINANTS

[76] Inventor: Derek James Whitehead, 103 Dickens Lane, Poynton, Cheshire, United Kingdom, SK12 1NT

[21] Appl. No.: 08/612,920

[22] PCT Filed: Jul. 11, 1995

[86] PCT No.: PCT/GB95/01627

§ 371 Date: Oct. 7, 1996

§ 102(e) Date: Oct. 7, 1996

[87] PCT Pub. No.: WO96/01619

PCT Pub. Date: Jan. 25, 1996

[30] Foreign Application Priority Data

Jul. 11, 1994 [GB] United Kingdom .................. 9413957

[51] Int. Cl.[7] ....................................................... A23K 1/18
[52] U.S. Cl. .......................... 424/438; 424/439; 424/442
[58] Field of Search .................................... 424/442, 438, 424/229, 408, 439, 475

[56] References Cited

U.S. PATENT DOCUMENTS

| 4,066,754 | 1/1978 | Chou | 424/229 |
| 4,578,263 | 3/1986 | Whitehead | 424/15 |
| 4,863,455 | 9/1989 | Whitehead | 604/890.1 |

*Primary Examiner*—Thurman K. Page
*Assistant Examiner*—William E. Benston, Jr.

[57] ABSTRACT

A bolus for delivery of pulsed doses of biologically active material to a ruminant comprises a series of distinct and separate bolus elements. Each bolus element is constructed of a degradable outer sheath and a core of biologically active material. The elements are adapted to separate following administration to the ruminant, and to disperse in the rumeno-reticular sac. In due course the elements degrade or corrode to release the biologically active material. Example boli include bolus elements of different respective corrosion characteristics and, as such, are capable of releasing pulsed doses of the active material to the ruminant.

19 Claims, 1 Drawing Sheet

6,030,637

PELLET FOR ADMINISTRATION TO RUMINANTS

This application is a 371 of PCT/GB95/01627, filed Jul. 11, 1995.

The present invention relates to pellets or boli for administration to ruminant animals and in particular to cattle and sheep. The invention particularly concerns boli intended to reside in the rumeno-reticular sac and to release predetermined quantities of one or more biologically active substances over an extended period of time.

The delivery of active agents to ruminant animals by administration of pellets or boli is a well established procedure having been practised for over thirty years. The boli are typically introduced into the rumeno-reticular sac via the mouth using a balling gun and remain there for a period of time which may extend to several months.

There are in general two types of boli in use. They are characterised according to (i) whether the active agent is released continuously with time, or (ii) is delivered as a series of pulses, separated by discrete periods of time during which the animal receives no active agent. Anthelmintics for the control of parasites are commonly administered by both types of bolus.

EP-A-0243111 and EP-A-0164927, for example, describe the construction of continuous release and pulse release boli respectively and boli described in these publications are commercially exploited. These patent applications disclose boli of generally elongate, cylindrical shape where the rate of drug release or the timing of that release is controlled by the rate of axial corrosion in the rumen juices of a magnesium alloy rod or tube. The rod/tube is disposed longitudinally in the bolus and coupled electrically to a cathodic element.

In the case of commercially available boli according to EP 0243111, the active agent is present in the bolus as an ingredient of weighted cathodic tablets contained within a magnesium alloy tube. The rate of corrosion of this tube determines the rate of erosion of the contained tablets, the active agent content of which is released continuously. In the example boli constructed in accord with EP 0164927, the drug is contained in the bolus as a plurality of discrete interlocking tablets disposed over an axial magnesium alloy rod and which carries an iron cathode at one end, the latter also serving as a weight. The animal's rumen juices degrade the alloy rod axially, over a period of time, to successively release the tablets.

In both cases the amount of benzimidazole required for a cattle bolus with a life of 120 days would be approximately 5–12 grams depending on the tyre of benzimidazole and the size of animal. This occupies a considerable volume and results in a bolus length which may extend to 9 cm. These boli deliver the active agent sequentially, the last doses of drug being released after the corrosion of some 5–9 cm length of magnesium alloy rod or tube.

Both types of release mechanism have their advantages. Pulse release may be preferred to continuous release on the grounds that it can result in the more economical use of an expensive active agent and may also prove less prone to conferring drug resistance to the parasites it is being employed against. However, it is generally more difficult to design and construct effective pulse release boli than is the case with continuous release. There is a need for a more simple and economical pulse release system than has hitherto been employed.

The present invention relates to a pulse release system which is simple and economical to construct and is particularly suited to the delivery of highly active agents such as avermectins where the quantity of anthelmintic required to control parasites is much smaller than is the case with benzimidazole or levamisole. However, the principles used may be applied to the pulse release of other active agents including growth promoters, trace elements, vitamins etc which are commonly administered to ruminant animals. Example active agents applicable to the present invention are disclosed in the aforementioned patent applications.

Thus, the present invention concerns a novel method of delivering active agents to a ruminant animal as a series of pulses by using several individual small bolus elements instead of a single bolus, each such bolus element being designed to release its quota of active agent after a specified period of time. All the bolus elements may conveniently be administered together at the start of treatment.

Accordingly, in one aspect the present invention provides a bolus for administration to a ruminant by deposition in its rumeno-reticular sac, the bolus comprising a plurality of discrete bolus elements, each element having a degradable outer sheath and a core of biologically active material, the elements being adapted to separate following administration to the animal. Thus, the bolus elements are capable of separating in use to disperse within the rumeno-reticular sac and subsequently release the biologically active material.

The present invention thus also concerns a generally elongate pellet or bolus which includes biologically active material accommodated in a degradable sheath which, in use, will degrade or corrode in the rumeno-reticular sac to release the biologically active material, characterised in that the bolus is made up of a plurality of independent and separate bolus elements, each said element providing a degradable sheath part and a portion of biologically active material for the bolus. The bolus elements, being generally independent, readily disperse in the rumen. In this respect the present invention is distinguished from the prior proposals referred to above which all relate to boluses which essentially remain in the rumen as a single entity, which is progressively eroded (usually from one end to the other, or perhaps from both ends to the centre). Thus, the provision of a plurality of bolus elements which are dispersible in use may be one of the characterising features of the present invention.

In other aspects the invention concerns such bolus elements, and a method of constructing bolus utilising such bolus elements.

Conveniently a bolus element has a density of from about 2.25 to 3.5 g/ml, preferably at least about 2.5 gm/ml so that it is retained by the animal for a reasonable period to allow for release of the biologically active material.

Preferably, a bolus element comprises a hollow sheath which conveniently includes a magnesium alloy component and an electrically conductive material cathodic to magnesium. Under the conditions of use of the present boli, the rumen liquor may serve as an electrolyte and the magnesium alloy may act as an anode when the bolus element is in the rumen. A core of the sheath suitably contains the biologically active material, which is typically of a material other than a magnesium alloy.

In preferred embodiments the sheath comprises a generally cylindrical cathode essentially closed by one or more anode plugs against undesired ingress of liquid. Suitably the cylindrical cathode has one open end which is closed by an anode plug. Conveniently, a cathode is in the form of a disc of generally circular or other shape and having a flange around its periphery which defines a cavity or pocket for accommodating a biologically active agent, and preferably also an anode plug. Thus, a bolus conveniently comprises a series of axially spaced cathodes, defining cavities between then, each cavity accommodating a biologically active material and an anode plug. Preferably the bolus elements are not arranged to interlock in any way with adjacent elements or any other parts of the bolus as this would inhibit the separation and dispersion of the elements.

A bolus element may be constructed so that essentially all the outer sheath will degrade in the rumen. This is desirable in many countries where abattoir equipment is employed to process carcases. Otherwise, it is possible that any hard remnants of the outer sheath may damage the processing equipment. Thus, in some embodiments a bolus element has an outer sheath which is constructed to be degradable in the rumen and without leaving hard residues or remnants.

In preferred embodiments such a degradable outer sheath comprises an anode part of a magnesium alloy and a cathode part comprising a pressed powder, preferably of iron and most preferably in admixture with graphite. In such embodiments both the anode part and cathode part are degradable.

In other embodiments a bolus element may be constructed so that only a part of the outer sheath is degradable in the rumen liquor, at least to an extent which is sufficient to expose and permit release of the core of biologically active material. Such example boli may find use in countries where automated abattoir processing equipment is not employed. In such embodiments, the outer sheath is typically constructed to include at least a degradable anode plug, preferably of a magnesium alloy. The cathode part may be constructed from various selected hard materials which are cathodic to magnesium, preferred materials being iron and copper based alloys.

In some embodiments it is desirable to improve the ability of the cathode material to withstand the abrasive effect of the rumen contents. In such cases the exterior surface of the cathode may be provided with a protective coating. Preferably the coating is not provided at or near to the area of the cathode which is adjacent to an anode plug. Preferred protective coatings include materials which are generally liquid impermeable, such as thin plastic materials e.g. polyvinylchloride. Conveniently, such coatings may be injection moulded. Example plastic coatings are described in the earlier patent applications referred to above.

Preferably, a bolus according to embodiments of the invention comprises a plurality of bolus elements contained in a degradable casing. Thus, the casing may degrade in the rumeno-reticular sac to allow the bolus elements to separate, in use. A preferred degradable casing includes paper, card or similar. The casing is suitably arranged to be a tight friction fit around the outer sheaths of the bolus elements to facilitate delivery of the pellet to the animal, but nevertheless readily disintegrates in the rumen juices so as not to unduly inhibit dispersion and separation of the bolus elements. A preferred casing is in the form of a helically wound tube of cardboard or paper, which is especially susceptible to being peeled away after being wetted by rumenal fluids.

In preferred embodiments the bolus includes two or more bolus elements having different respective degradation or corrosion characteristics. Preferably the bolus includes at least two elements which contain anodes having different respective corrosion characteristics. In particularly preferred embodiments a bolus includes at least two element comprising anodes of different respective magnesium alloys. For example the alloys may include different constituents or perhaps different ratios of selected constituents. Alternatively, or in addition, a bolus preferably includes at least two anodes and/or cathodes of different respective volumes and/or surface areas. In particularly preferred embodiments the bolus elements comprise similar cathodes but differ in the nature of their anodes.

It will be appreciated that the present boli may include further components in addition to the bolus elements described above. Preferably, however, the present boli will consist essentially of the bolus elements generally accommodated in a casing which will degrade in the rumen. Also, a bolus may include any number of bolus elements as appropriate, and each bolus element may accommodate one or more biologically active ingredients.

As noted above, in another broad aspect the present invention provides a method of manufacturing boli for administration to ruminants, the method comprising providing a plurality of discrete bolus elements, each said element including a degradable outer sheath and a core of biologically active material, and optionally encasing the bolus elements in a degradable casing, and preferably selecting two or more bolus elements of different respective corrosion characteristics for accommodation in the casing.

In yet another aspect the present invention provides a method for administering pulsed doses of biologically active materials to ruminants which method involves the essentially simultaneous supply of a plurality of bolus elements, each said element including a degradable outer sheath and a core of biologically active material, the respective elements being adapted to have different respective degradation-characteristics so as to release the biologically active material at different respective intervals.

Figure 1:
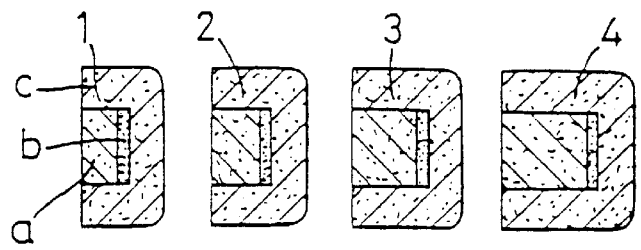
FIG. 1 illustrates longitudinal cross-sections of four cylindrical bolus elements.

Embodiments of the present invention will now be described further, by way of example, with reference to the accompanying FIGS. 1 to 5, which each show a longitudinal cross-section of an example bolus.

EXAMPLES

A typical bolus element according to embodiments of the present invention comprises three parts. The first part is an outer component, generally cylindrical in shape, made from an electrically conductive material cathodic to magnesium, and of such a density that the bolus element has a density of at least 2.5 gm/ml. The material from which the outer component, or cathode, is made should be sufficiently hard and mechanically strong to withstand the abrasive effect of the rumen contents. If this is not the case then the exterior faces of the cathode (apart from the area adjacent to the anode, described in more detail below) may be covered or encased in a thin plastic shell which may conveniently be injection moulded.

The outer component has a cylindrical cavity, the innermost end of which contains a quantity of the second component i.e. the active agent, which in the case of solid materials may be in the form of a generally cylindrical tablet.

The active agent is initially sealed from the rumen contents by means of a third component, comprising a magnesium alloy plug which acts as an anode and which closes the outermost end of the cylindrical hole of the first component. When exposed to the rumen juices the magnesium alloy plug corrodes gradually by galvanic action until the drug is exposed when the active agent is released to the animal.

The time taken to release an active agent may be varied from a few hours to a period-of months by several means e.g.

1. By Altering the Composition of the Magnesium Alloy Plug

Magnesium alloys containing heavy metals such as copper, nickel, lead, silver, tin, cerium, cobalt, iron and zirconium may be used to make plugs with higher corrosion rates.

Many commercial magnesium based alloys contain aluminium as a major alloying element. The presence of aluminium improves the mechanical properties and fabrication qualities of magnesium. Low aluminium contents favour low corrosion rates in the rumen.

Manganese containing magnesium base alloys as disclosed in EP-A-0482947 have especially low corrosion rates in the rumen and also find application with this invention.

2. By Varying the Cathode Material

The corrosion potential between magnesium and a cathode when immersed in rumen liquor varies with the type of cathode as shown in Table 1,

TABLE 1

| Coupling Material | Corroding Potential (Volts) |
| --- | --- |
| Copper | 1.6 |
| Graphite | 1.5 |
| Iron | 1.0 |
| Zinc | 0.6 |
| Aluminium | 0.5 |

The higher the potential the greater the rate of corrosion of the magnesium alloy plug. The choice of cathode material is not limited to the above examples and includes alloys of different elements and compacts of different materials produced by powder metallurgy techniques.

3. By Altering the Relative Areas of Anode and Cathode Exposed to the Rumen Contents The higher the ratio of cathode area/anode area the greater the rate of corrosion of the magnesium alloy plug.

It will be seen from the above that the invention offers great scope for varying the time taken for the active agent contained in the bolus segment to be released in the rumen and by several means.

Various example boli constructions are illustrated in the accompanying drawings in which:

FIG. 1 shows longitudinal cross-sections of four cylindrical bolus elements (1, 2, 3, 4). For each element, a drug tablet b is contained within the dense cathodic sheath c and is initially sealed from contact with the rumen contents by a cylindrical magnesium anode a which is a close fit in sheath c. When administered to the animal galvanic corrosion of the magnesium plug progressing from the exterior of the bolus element eventually results in exposure of the drug tablet b to the rumen juices and release of active agent in the tablet b. The four bolus elements depicted in FIG. 1 illustrate how the time taken to release the drug may be varied by altering the length of the anodic plug.

In more detail, in an example bolus typically the outer sheath c, will be about 20 mm in diameter and contain a magnesium alloy anode plug of about 5–7 mm diameter. The outer sheath is made from a 50—50 mixture of pure iron and graphite powders each of 100–300 mesh size. The respective powders are intimately mixed and die pressed in a hydraulic or mechanical press at a direct load of 10 tonnes. Generally, such compacts of graphite and iron are sufficiently hard and strong to substantially retain their integrity in the rumen for the intended life of the bolus e.g. normally up to about 140 days. Thereafter they may gradually erode away by action between individual boli elements and with the rumen contents. However the cathode sheaths will usually be designed to be not sufficiently hard as to damage abattoir equipment used to process carcases. It will be appreciated that if this is not a consideration then boli cathode sheaths can be made from a variety of hard materials cathodic to magnesium e.g. iron and copper base alloys and manufactured by machining from the solid or by standard powder metallurgy and sintering techniques or directly by shape casting from liquid metal e.g. by gravity or pressure diecasting.

A 7 mm diameter cylindrical plug, diecast or extruded from the commonly used veterinary alloy MAB1 containing 12%-aluminium, 2% copper, remainder magnesium alloy corrodes linearly in the rumen of a 200 kg heifer at grass, at the rate of approximately 0.5 mm per day. Varying the length of the anode plugs shown in FIG. 1 hence allows the administration of predetermined drug pulses to the animal. The anode plugs are made a close fit in the cathodic sheath to avoid the ingress of fluid at the interface of anode and cathode.

The tablet containing the active agent is made using standard formulation and manufacturing techniques well known to those skilled in the art. It is advisable that the tablet should disintegrate reasonably quickly when exposed to the rumen liquor. For example a tablet designed to deliver a therapeutic pulse dose of abermectin may contain:

80 mg abamectin 40 mg starch 5 mg polyvinylpyrolydene 2 mg magnesium stearate 25 mg lactose A wide variety of diluents may be used with the commonly used anthelmintics of the benzimidazole type and avermectins to form suitable degradable tablets. Graphite may also be advantageously employed as a constituent of such tablets where it is desirable that the tablet should preserve an electrically conductive path between anode plug and cathode sheath. The tablet is inserted in the cathode sheath cavity prior to pressing in the anode plug.

Figure 2:
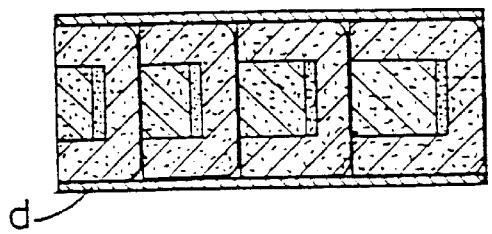
FIG. 2 illustrates the bolus elements of FIG. 1 in a degradable sleeve.

FIG. 2 shows how the bolus elements of FIG. 1 may be contained in a degradable sleeved for ease of administration. The sleeve d may be constructed from paper, card or other material easily degraded in the rumen to release the individual boli within a short time after introduction of the assembly to the rumen. The sleeve shown in FIG. 2 is made from thin paper card approximately 2 mm thick.

Figure 3:
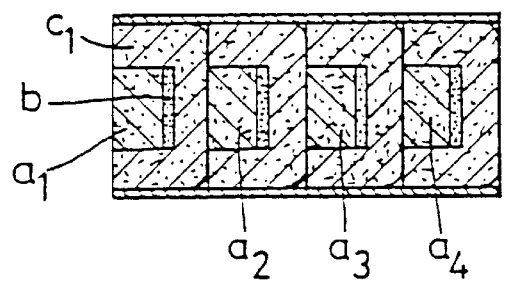
FIG. 3 illustrates four bolus elements having identical cathodic sheaths.

FIG. 3 shows four bolus elements which for ease of manufacture have identical cathodic sheaths. The magnesium alloy plugs a1, a2, a3, and a4 are constructed however from alloys or metals with different corrosion characteristics.

The anode plugs shown in FIG. 3 may be made from alloys of the magnesium-aluminium-copper-manganese type. High copper contents e.g. up to 5% promote high corrosion rates. High aluminium contents e.g. up to 12% are also associated with more rapid corrosion. Absence of copper and inclusion of manganese up to 1% yields alloys with very low corrosion rates in the rumen even when electrically coupled to carbon, copper or iron. It is hence feasible for one skilled in the art to construct cathode sheaths and anode plugs from appropriate alloys whose composition is determined by the corrosion rate required. As an example a 7 mm anode plug made from a magnesium, 9% aluminium, 1% copper, 0.2% manganese alloy corrodes in the rumen when coupled to a graphitic cathode sheath at approximately 60% of the rate of a similar MAB1 alloy plug.

Figure 4:
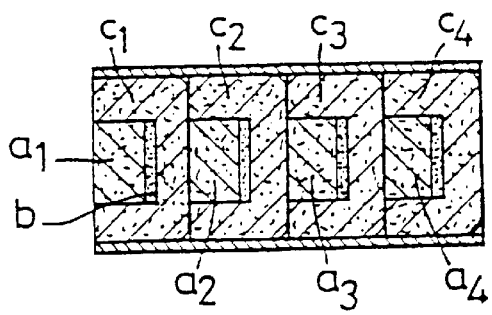
FIG. 4 illustrates a bolus element construction having two different types of cathodic sheaths.

FIG. 4 shows bolus element construction where two different types of cathodic sheath c1, and c2 are used, each sheath containing a different anodic plug a1, a2, a3 and a4.

Figure 5:
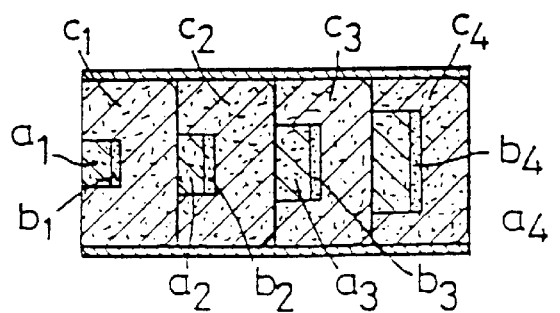
FIG. 5 illustrates bolus elements having varying anode/cathode area ratios.

FIG. 5 shows bolus elements with varying anode/cathode area ratios. It will be appreciated that the time taken to release the drug tablet b4 will be longer than that required for b1 due to the lower current density at a4 compared with a1. It should be noted that this design of bolus element allows an increasing quantity of active agent to be released with time. This is an advantage when with increasing bodyweight of the animal with time a higher quantity of active agent is required to give an adequate dose. However, some parasitic corrosion of the magnesium anode does occur, the rate of which is independent of the relative anode cathode areas. The more reactive the alloy the higher the parasitic corrosion element. This method of controlling bolus life is hence less effective and predictable than those illustrated above.

The weight and dimensions of an example of bolus may vary according to the particular materials used for the bolus and according to the particular ruminant.

It will be appreciated that by using different combinations of anode material, anode length, cathode material and varying anode cathode area ratios, it is possible to construct bolus elements with widely varying release times extending from a few days to several months. This gives a flexibility of bolus design which has hitherto not been available.

Various modifications may be made to the illustrated embodiments.

I claim:

1. A bolus for administration to a ruminant by deposition in its rumeno-reticular sac, the bolus comprising a plurality of discrete bolus elements, each said element having a degradable outer sheath including one or more cathode parts and one or more anode parts and a core of biologically active material, the elements being adapted to separate and disperse within the rumeno-reticular sac following administration to the animal and to subsequently corrode to release biologically active material.

2. A bolus according to claim 1 wherein the degradable outer sheath of a bolus element comprises a hollow cylindrical sheath which is closed at both ends.

3. A bolus according to claim 1 wherein a bolus element comprises a degradable anode part and a degradable cathode part.

4. A bolus according to claim 1 wherein only part of the outer sheath of a bolus element is constructed so as to be degradable in the rumeno-reticular sac.

5. A bolus according to claim 4 wherein a bolus element includes an outer sheath in which only the anode part is degradable in the rumeno-reticular sac.

6. A bolus according to claim 1 wherein the degradable outer sheath of a bolus element includes a magnesium alloy as an anode part and a cathode part comprising an electrically conductive material cathodic to magnesium.

7. A bolus according to claim 6 wherein the cathode part comprises pressed iron and graphite powders.

8. A bolus according to claim 1 wherein the degradable outer sheath of a bolus element comprises a cylindrical cathode closed by one or more anode plugs.

9. A bolus according to claim 8 wherein the cylindrical cathode has one open end which is closed by an anode plug.

10. A bolus according to claim 9 wherein the cathode is in the form of a disc having a flange around its periphery which defines a cavity for accommodating a biologically active agent and one or more anode plugs.

11. A bolus according to claim 1 wherein an exterior surface of the cathode of a bolus element is provided with a liquid impermeable protective coating.

12. A bolus according to claim 1 comprising a plurality of bolus elements contained in a casing which is adapted to degrade in the rumeno-reticular sac, in use, to allow the bolus elements to separate.

13. A bolus according to claim 1 including two or more bolus elements having different respective corrosion characteristics.

14. A bolus according to claim 13 including two or more bolus elements, each element containing an anode having different respective corrosion characteristics.

15. A bolus according to claim 13 including two or more bolus elements having anodes of different respective magnesium alloys.

16. A bolus according claim 13 including two or more bolus elements which differ in respect of the volumes and/or surface areas of their respective anodes.

17. A bolus according to claim 13 including two or more bolus elements which differ in respect of the volumes and/or surface areas of their respective cathodes.

18. A method of manufacturing a bolus, the method comprising constructing a plurality of discrete bolus elements, each said element having a degradable outer sheath including one or more cathode parts and one or more anode parts and a core of biologically active material, and selecting two or more bolus elements in accordance with their respective corrosion characteristics and combining the elements to provide a bolus.

19. A method according to claim 18 in which the step of combining the bolus elements further comprises providing a degradable casing for the elements.

* * * * *